(12) United States Patent
Wu et al.

(10) Patent No.: US 9,691,256 B2
(45) Date of Patent: Jun. 27, 2017

(54) METHOD AND DEVICE FOR PRESENTING PROMPT INFORMATION THAT RECOMMENDS REMOVING CONTENTS FROM GARBAGE CONTAINER

(71) Applicant: Xiaomi Inc., Beijing (CN)

(72) Inventors: Ke Wu, Beijing (CN); Xinyu Liu, Beijing (CN)

(73) Assignee: Xiaomi Inc., Beijing (CN)

( * ) Notice: Subject to any disclaimer, the term of this patent is extended or adjusted under 35 U.S.C. 154(b) by 0 days.

(21) Appl. No.: 15/137,545

(22) Filed: Apr. 25, 2016

(65) Prior Publication Data

US 2016/0379468 A1  Dec. 29, 2016

(30) Foreign Application Priority Data

Jun. 26, 2015  (CN) .......................... 2015 1 0364123

(51) Int. Cl.
*B65F 1/00* (2006.01)
*G08B 21/24* (2006.01)
*G08B 21/12* (2006.01)
*G08B 3/10* (2006.01)
*H04M 1/725* (2006.01)
*G01N 21/25* (2006.01)
(Continued)

(52) U.S. Cl.
CPC ............... *G08B 21/24* (2013.01); *B65F 1/14* (2013.01); *G01N 21/255* (2013.01); *G01N 33/0001* (2013.01); *G08B 3/10* (2013.01); *G08B 21/12* (2013.01); *H04M 1/72569* (2013.01); *B65F 2210/128* (2013.01); *B65F 2210/168* (2013.01); *G01N 2201/12* (2013.01)

(58) Field of Classification Search
CPC ................................................. B65F 2210/168
USPC ..................................... 340/539.26, 539, 22
See application file for complete search history.

(56) References Cited

U.S. PATENT DOCUMENTS 6,425,487 B1   7/2002   Emmott et al.
9,102,465 B2   8/2015   Davis
(Continued)

FOREIGN PATENT DOCUMENTS

CN    101482742 A    7/2009
CN    103043347 A    4/2013
(Continued)

OTHER PUBLICATIONS

International Search Report issued Apr. 1, 2016 for International Patent Application No. PCT/CN2015/098976.
(Continued)

*Primary Examiner* — Kevin Kim
(74) *Attorney, Agent, or Firm* — Oblon, McClelland, Maier & Neustadt, L.L.P.

(57) ABSTRACT

Aspects of the disclosure provide a method for presenting prompt information that recommends removing contents from a garbage container. The method includes acquiring garbage information and garbage decaying benchmark information of the contents in the garbage container; determining whether the contents in the garbage container have mold or odor based on the garbage information and the garbage decaying benchmark information; and presenting the prompt information that recommends removing the contents from the garbage container when it is determined that the contents in the garbage container have mold or odor.

20 Claims, 10 Drawing Sheets

(51) Int. Cl.
*G01N 33/00* (2006.01)
*B65F 1/14* (2006.01)

(56) References Cited

U.S. PATENT DOCUMENTS

| | | | |
|---|---|---|---|
| 2009/0161907 A1 | 6/2009 | Healey et al. | |
| 2014/0214697 A1* | 7/2014 | McSweeney | B65F 1/004 705/308 |
| 2015/0040625 A1 | 2/2015 | Devine et al. | |
| 2015/0095103 A1* | 4/2015 | Rajamani | G06Q 30/0201 705/7.29 |
| 2015/0323366 A1* | 11/2015 | Kekalainen | G01D 11/30 702/188 |
| 2015/0350610 A1* | 12/2015 | Loh | H04N 7/183 348/143 |

FOREIGN PATENT DOCUMENTS

| | | |
|---|---|---|
| CN | 103231881 A | 8/2013 |
| CN | 103577922 A | 2/2014 |
| CN | 203790733 U | 8/2014 |
| CN | 104147630 A | 11/2014 |
| CN | 203959064 U | 11/2014 |
| CN | 204110684 U | 1/2015 |
| CN | 104648861 A | 5/2015 |
| CN | 104709648 A | 6/2015 |
| CN | 104909091 A | 9/2015 |
| DE | 42 23 088 A1 | 1/1994 |
| ES | 2 117 567 | 8/1998 |
| WO | WO 2013/163362 A1 | 10/2013 |

OTHER PUBLICATIONS

Combined Office Action and Search Report issued May 27, 2016 in Chinese Patent Application No. 201510364123.8 (with Partial English Translation and English Translation of Categories of Cited Documents).

Combined Office Action and Search Report issued Jan. 22, 2017 in Chinese Patent Application No. 201510364123.8 (with Partial English Translation and English Translation of Categories of Cited Documents).

Extended European Search Report issued Nov. 14, 2016 in Patent Application No. 16173752.3.

Russian Office Action dated Feb. 28, 2017, issued in Russian Patent Application No. 2016110466/12(016491) (with English translation).

* cited by examiner

METHOD AND DEVICE FOR PRESENTING PROMPT INFORMATION THAT RECOMMENDS REMOVING CONTENTS FROM GARBAGE CONTAINER

CROSS-REFERENCE TO RELATED APPLICATION

This application bases on and claims priority of the Chinese Patent Application No. 201510364123.8 filed on Jun. 26, 2015, which is incorporated by reference in its entirety.

TECHNICAL FIELD

The present disclosure generally relates to the field of communication technology, and more particularly, to method and device for presenting prompt information that recommends removing contents from a garbage container.

BACKGROUND

With the rapid development of the economy and the quick improvement of standard of living, great amounts of garbage have been generated daily at home and in the factories. People typically keep garbage in a garbage container, into which a garbage bag is placed to hold the garbage. In some applications when there is too much garbage in the garbage bag, the bag will be removed from the garbage container.

When a lot of garbage is placed into a garbage container for an extended period of time, mold or odor will grow due to the decomposition of the garbage. The mold and odor not only significantly affect human health but also pollute the environment.

SUMMARY

Aspects of the disclosure provide a method for presenting prompt information that recommends removing contents from a garbage container. The method includes acquiring garbage information and garbage decaying benchmark information of the contents in the garbage container; determining whether the contents in the garbage container have mold or odor based on the garbage information and the garbage decaying benchmark information; and presenting the prompt information that recommends removing the contents from the garbage container when it is determined that the contents in the garbage container have mold or odor.

In an embodiment, acquiring garbage decaying benchmark information includes acquiring a garbage type of the contents in the garbage container; and acquiring the garbage decaying benchmark information corresponding to the garbage type.

In an embodiment, acquiring the garbage type of the contents in the garbage container includes acquiring the garbage type by scanning a barcode on a packing box or on a packing bag in the contents; or acquiring the garbage type by identifying the contents via a camera; or acquiring the garbage type by performing a spectroscopic analysis on composition of the contents; or receiving the garbage type reported by the garbage container.

In an embodiment, acquiring garbage decaying benchmark information corresponding to the garbage type includes querying a database based on the garbage type to acquire garbage decaying benchmark information corresponding to the garbage type, the database storing decaying benchmark information of different garbage types; or acquiring garbage decaying benchmark information corresponding to the garbage type from stored history record information; or acquiring garbage decaying benchmark information corresponding to the garbage type based on user's review information.

In an embodiment, acquiring the garbage information of the contents in the garbage container includes acquiring garbage image information of the contents in the garbage container via a camera; or acquiring garbage smell information of the contents in the garbage container via a smell sensor.

In an embodiment, determining whether the contents in the garbage container have mold or odor includes determining whether the garbage information is consistent with at least a part of the garbage decaying benchmark information.

Aspects of the disclosure provide a device for presenting prompt information that recommends removing contents from a garbage container. The device includes a processor and a memory storing instructions executable by the processor. The processor is configured to acquire garbage information and garbage decaying benchmark information of the contents in the garbage container, determine whether the contents in the garbage container have mold or odor based on the garbage information and the garbage decaying benchmark information, and present the prompt information that recommends removing the contents from the garbage container when it is determined that the garbage have mold or odor.

In an embodiment, the processor is configured to acquire a garbage type of the contents in the garbage container, and acquire garbage decaying benchmark information corresponding to the garbage type.

In an embodiment, when determining whether the contents in the garbage container have mold or odor, the processor is configured to determine whether the garbage information is consistent with at least a part of the garbage decaying benchmark information.

BRIEF DESCRIPTION OF THE DRAWINGS

The accompanying drawings, which are incorporated in and constitute a part of this specification, illustrate embodiments consistent with the present disclosure and, together with the description, serve to explain the principles of various embodiments of the present disclosure.

DETAILED DESCRIPTION

Reference will now be made in detail to exemplary embodiments, examples of which are illustrated in the accompanying drawings. The following description refers to the accompanying drawings in which same numbers in different drawings represent same or similar elements unless otherwise described. The implementations set forth in the following description of exemplary embodiments do not represent all implementations consistent with the present disclosure. Instead, they are merely examples of apparatuses and methods consistent with aspects related to the present disclosure.

Figure 1:
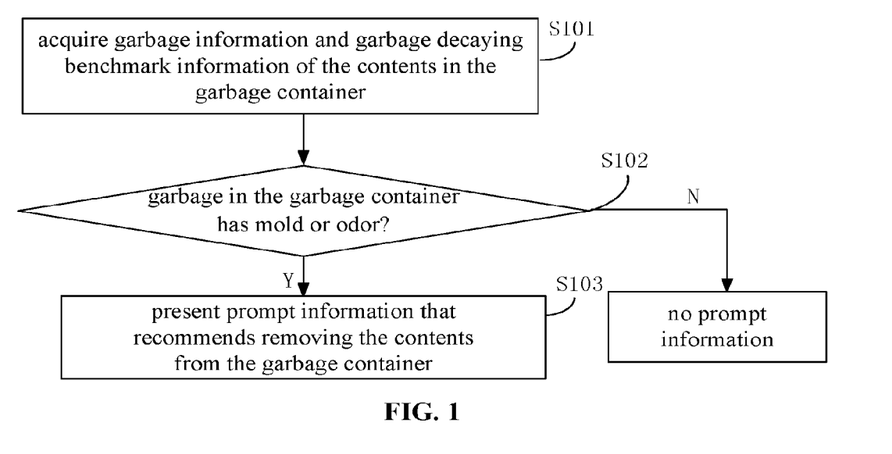
FIG. 1 is a flow chart showing a method for presenting prompt information that recommends removing contents from a garbage container according to an exemplary embodiment.

FIG. 1 is a flow chart showing a method for presenting prompt information that recommends removing contents from a garbage container according to an exemplary embodiment. As shown in FIG. 1, the method for presenting prompt information that recommends removing contents from a garbage container may be applied to a mobile terminal, which may be a terminal device, such as a phone, a PAD, etc., capable of accessing the Internet. The method may include the following steps S101-S103.

In step S101, garbage information and garbage decaying benchmark information of the contents (i.e., also referred to as garbage in the present disclosure) in the garbage container may be acquired. In some embodiments, a garbage bag is placed in the garbage container to hold the contents.

In the embodiment, a mobile terminal such as a phone may acquire a garbage type of the garbage in the garbage container and acquire garbage decaying benchmark information corresponding to the garbage type.

The mobile terminal such as a phone may acquire the garbage type decomposition benchmark in, but not limited to, the following ways.

The first way is by scanning a barcode on a packing box or on a packing bag in the contents.

The second way is by identifying the contents via a camera.

The third way is by performing a spectroscopic analysis on composition of the contents.

The fourth way is by receiving the garbage type reported by the garbage container, where the garbage type reported by the garbage container may be acquired by the garbage container in one or more of the first to third ways advanced above.

The mobile terminal such as a phone may acquire garbage decaying benchmark information corresponding to the garbage type in, but not limited to, the following ways: it may query a database based on the garbage type to acquire garbage decaying benchmark information corresponding to the garbage type, the database storing decaying benchmark information of different garbage types; it may acquire garbage decaying benchmark information from stored history record information; or it may acquire garbage decaying benchmark information corresponding to the garbage type based on user's review information.

As can be seen, the present embodiment may acquire garbage decaying benchmark information in flexible and diverse ways.

Meanwhile, garbage image information of the garbage in the garbage container may be acquired via a camera, and garbage smell information of the garbage in the garbage container may be acquired via a smell sensor.

As important to note, the garbage container mentioned in the present embodiment is a smart garbage can with communication functions.

In step S102, whether the garbage in the garbage container have mold or odor may be determined based on the garbage information and the garbage decaying benchmark information.

In the embodiment, whether garbage in the garbage container has produced mold or odor may be determined by determining whether the garbage information is consistent with at least a part of the garbage decaying benchmark information, wherein the garbage decaying benchmark information is used to determine whether the garbage in the garbage container have mold or odor.

For example, picture information acquired may be compared with picture information of garbage on which mold has grown to a predetermined extent; and if their matching degree is higher than a preset value, it is determined that the garbage in the garbage container has mold.

In step S103, when it is determined that the garbage in the garbage container has mold or odor, the prompt information that recommends removing the garbage from the garbage container is presented to a user to remind the user to clear the contents of the garbage container by, for example, removing the garbage bag that holds the garbage in the garbage container.

The mobile terminal may determine whether the garbage in the garbage container has mold or odor present and determine whether to present the prompt information that recommends removing contents from a garbage container to the user accordingly.

However, in some cases such as when the user is going to a toilet, the smell sensor may detect that a garbage container beside the toilet has odor and report the odor information to the mobile terminal. However, at this time, the odor as picked up by the smell sensor is in fact dominated by the odor of the toilet, and presenting the prompt information would be deemed as a false alarm due to misjudgments. In order to avoid such a situation, before sending the prompt information that recommends removing contents from a garbage container to the user, the method may further include: acquiring behavior information of the user and the distance between the user and the garbage container; determining whether the distance is smaller than a predetermined threshold and whether the behavior information is in a predetermined list; when it is determined that the distance is smaller than the predetermined threshold and the behavior information is in the predetermined list, not sending the user the prompt information; and sending the user the prompt information for changing the garbage bag in all other cases. In some embodiments, the predetermined list is used to store information of a behavior that can produce odor. In some embodiments, behavior information of the user may be collected by a wearable device such as bracelet, and distance information may be acquired based on Bluetooth signal intensity information.

As can be seen, the above way can effectively reduce situations in which prompt information is sent to a user due to misjudgments, thus effectively reduces interruption to users and improves the degree of use experience of the user.

In the present embodiment, the mobile terminal may send the user the prompt information for changing the garbage bag in the following one or more ways: it may directly display the prompt information that recommends removing contents from a garbage container via the mobile terminal. In some embodiments, the method may include issuing an alert to prompt the user to read the prompt information on the mobile terminal via a wearable device such as a bracelet. In some embodiments, the method may also include sending the garbage container a first instruction when it is detected that the user has come back home, which instruction is used to control the garbage container to present the prompt information; that is, the garbage container makes a sound prompt after receiving the first instruction. In some embodiments, the method may also include displaying the prompt information that recommends removing the contents from the garbage container via a terminal device, such as a TV, other than the user's mobile device when it is detected that the user has come back home. As can be seen, the present embodiment may send the user the prompt information that recommends removing the contents from the garbage container in flexible and diverse ways.

Wherein, the way to detect that the user has come back home may be detecting that the mobile terminal is in the same local area network as the garbage container, or detecting that the distance with the garbage container obtained via a Bluetooth signal intensity detection is within a preset range, etc.

Figure 2:
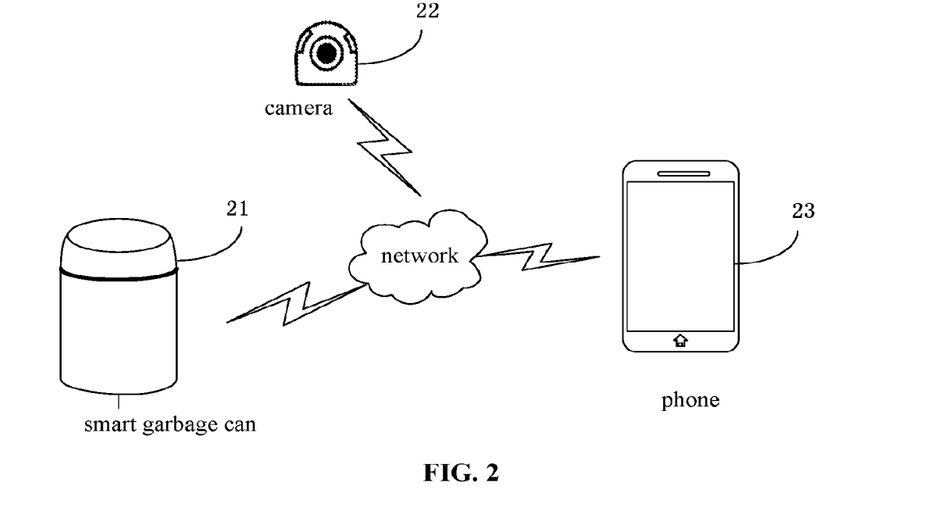
FIG. 2 is a system diagram showing a scenario where the method for presenting prompt information that recommends removing contents from a garbage container is performed according to an exemplary embodiment.

Below, the present disclosure is illustrated with reference to FIG. 2. As shown in FIG. 2, when a user is using a smart garbage container 21, the user may make a spectroscopic analysis on composition of the garbage to be placed into the smart garbage container 21 via a spectrometer in the smart garbage container 21 so as to acquire a garbage type (assumed as type A), and query a database such as a database of an online shopping site based on garbage of type A to acquire garbage decaying benchmark information of the garbage of type A. Then, garbage image information in the garbage container may be acquired via a camera 22, and the garbage image information and corresponding garbage decaying benchmark information may be compared by a phone 23. If it is found that the matching degree between the garbage image information and image information of garbage which has mold is higher than 90%, prompt information that recommends removing contents from a garbage container may be displayed on the phone 23, upon seeing which, the user will change the garbage bag timely, so that pollution of surrounding environment is reduced and use experience of the user is improved.

With the above embodiment of the method for presenting prompt information that recommends removing contents from a garbage container, by acquiring garbage information and garbage decaying benchmark information in a garbage container, determining whether garbage in the garbage container has mold or odor based on the garbage information and the garbage decaying benchmark information, and sending a user prompt information that recommends removing contents from a garbage container when it is determined that the garbage has mold or odor. Therefore, the impact on human health and the pollution of surrounding environment by garbage container be reduced effectively and use experience of the user can be improved since the embodiment prompts user to timely change the garbage bag when it is determined that garbage has mold or odor.

Figure 3:
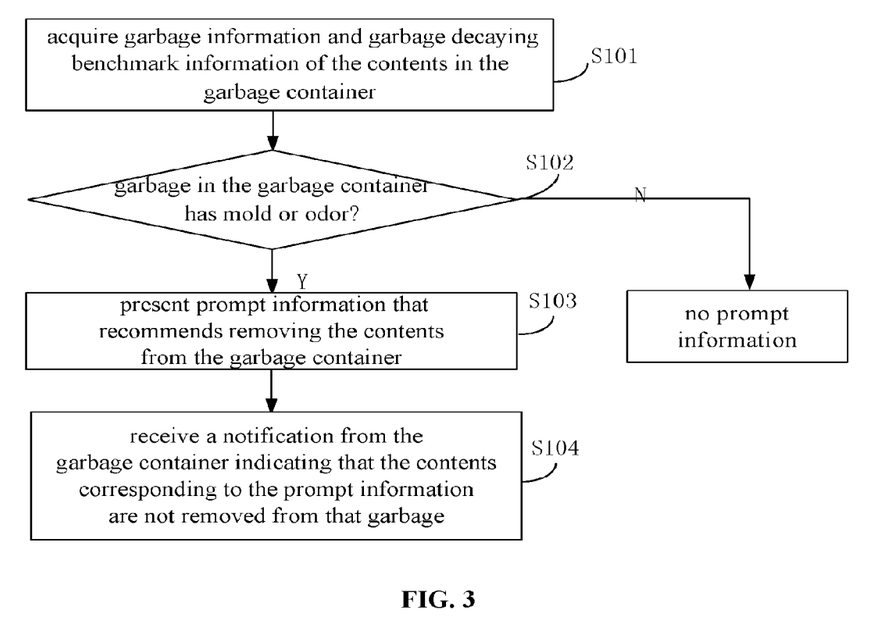
FIG. 3 is a flow chart showing another method for presenting prompt information that recommends removing contents from a garbage container according to an exemplary embodiment.

FIG. 3 is a flow chart showing another method for presenting prompt information that recommends removing contents from a garbage container according to an exemplary embodiment. As shown in FIG. 3, based on the embodiment shown in FIG. 1, the present embodiment may further include the following steps.

In step S104, a notification sent by the garbage container indicating that the contents corresponding to the prompt information have not been removed may be received and a second instruction used to control a smart device to handle the contents, such as to seal the garbage bag or remove the garbage bag, may be sent to the smart device.

In the present embodiment, after the mobile terminal such as a phone sends the user the prompt information that recommends removing contents from a garbage container in various ways, if the garbage container detects that the weight of the garbage has not changed and still has mold or odor within a preset time period such as one hour, it can be confirmed that the user has not clear the garbage container. Then, the garbage container may send the mobile terminal a notification indicating that the contents corresponding to the prompt information have not been removed, upon receipt of which, the mobile terminal may send a second instruction to a smart device in the same local area network such as a robot. After receiving the second instruction, the smart device may take predetermined actions in order to handle the contents based on predetermined, such as to seal the garbage bag or remove the garbage bag.

With the above embodiment of the method for prompting change of garbage bag, by sending a smart device a second instruction to enable the smart device to seal the garbage bag or drop the current garbage bag after receiving garbage-bag-unchanged prompt information sent by the garbage container, a situation in which garbage pollutes the environment due to a user forgetting to change a garbage bag can be prevented effectively.

Figure 4:
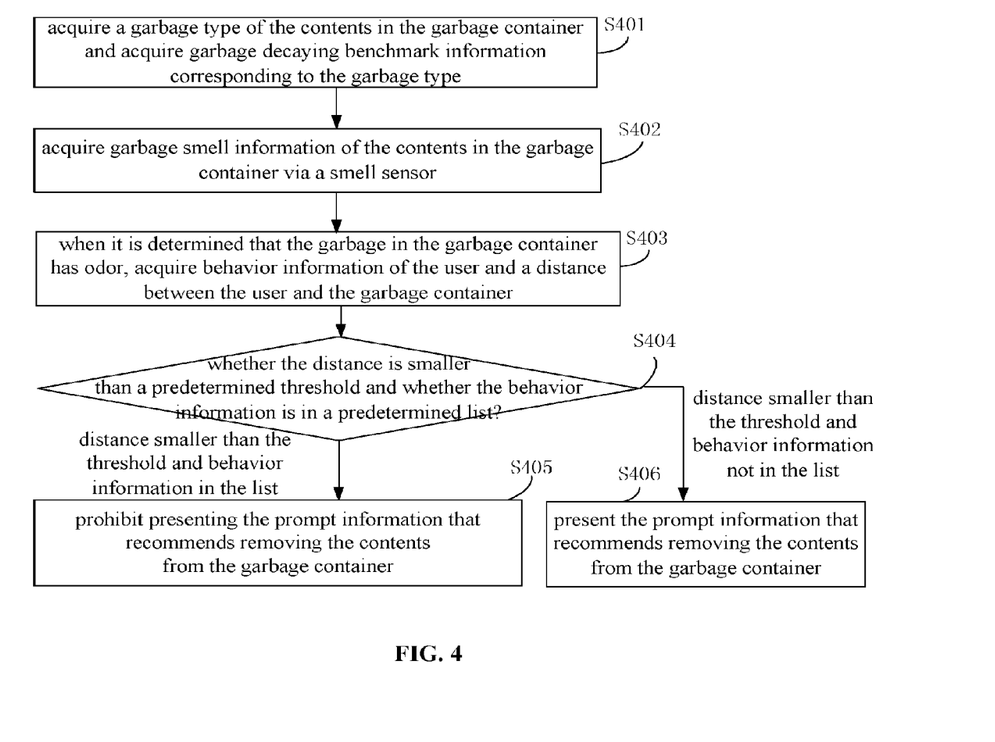
FIG. 4 is a flow chart showing another method for presenting prompt information that recommends removing contents from a garbage container according to an exemplary embodiment.

FIG. 4 is a flow chart showing another method for presenting prompt information that recommends removing contents from a garbage container according to an exemplary embodiment, which embodiment may be applied to a phone. As shown in FIG. 4, the method may include the following steps S401-S405.

In step S401, a garbage type of the contents in a garbage container may be acquired and garbage decaying benchmark information corresponding to the garbage type may be acquired.

Implementation of the above step may be acquired by referring to the corresponding part of the embodiment shown in FIG. 1, which will not be described in detail herein.

In step S402, garbage smell information in the garbage container may be acquired via a smell sensor.

In step S403, when it is determined that the garbage in the garbage container has produced odor, behavior information of the user and a distance between the user and the garbage container may be acquired.

In step S404, whether the distance is smaller than a predetermined threshold and whether the behavior information is in a predetermined list may be determined.

In some embodiments, the preset predetermined is used to store information of a behavior that can produce odor, such as cooking behavior information.

In step S405, when it is determined that the distance is smaller than the predetermined threshold and the behavior information is in the predetermined list, prompt information that recommends removing contents from a garbage container may not be sent to the user; and operation ends.

For example, when cooking, a user will typically drop fish debris, etc. into a garbage container, and the garbage container will detect a fishy smell. However, since the distance between the user and the garbage container is less than a predetermined distance, such as five meters, and the cooking behavior information of the user is in a predetermined list, prompt information that recommends removing contents from a garbage container will not be sent to the user. In such cases, the user typically needs to remove contents from the garbage container after cooking.

In step S406, when it is determined that the distance is smaller than the predetermined threshold and the behavior information is not in the predetermined list, prompt information that recommends removing contents from a garbage container may be sent to the user.

If determining that the distance between the user and the garbage container is less than a predetermined distance such as five meters but the cooking behavior information of the user is not in the predetermined list (for example, the user is pouring water in the kitchen), prompt information that recommends removing contents from a garbage container will be sent to the user.

In other cases, such as when the distance is larger than the predetermined distance, prompt information that recommends removing contents from a garbage container will also be sent to the user.

With the above embodiment of the method for presenting prompt information that recommends removing contents from a garbage container, when garbage smell information and garbage decaying benchmark information in the garbage container are acquired and it is determined that the garbage in the garbage container has produced odor based on the garbage smell information and garbage decaying benchmark information, by further acquiring behavior information of the user and a distance between the user and the garbage container and determining whether it is needed to send prompt information to a user based on this information. Accordingly, situations in which prompt information is sent to a user due to misjudgments can be effectively reduced so that interruption to users can be reduced effectively. Meanwhile, the impact on human health and the pollution of surrounding environment by garbage container be reduced effectively and use experience of the user can be improved.

Corresponding to above embodiments of methods for prompting change of garbage bag, the present disclosure further provides embodiments of devices for presenting prompt information that recommends removing contents from a garbage container.

Figure 5:
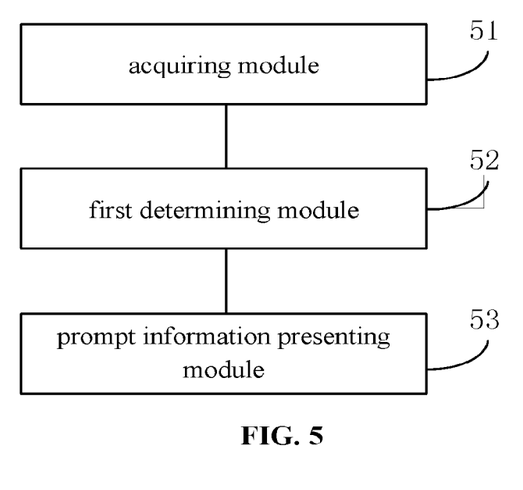
FIG. 5 is a block diagram showing a device for presenting prompt information that recommends removing contents from a garbage container according to an exemplary embodiment.

FIG. 5 is a block diagram showing a device for presenting prompt information that recommends removing contents from a garbage container. As shown in FIG. 5, the device for prompting change of garbage bag may include: an acquiring module 51, a first determining module 52 and a prompt information presenting module 53.

The acquiring module 51 may be configured to acquire garbage information and garbage decaying benchmark information in a current garbage bag.

The first determining module 52 may be configured to determine whether garbage in the garbage container has mold or odor based on the garbage information and the garbage decaying benchmark information acquired by the acquiring module 51.

The first determining module 52 may be configured to determine whether the garbage information is consistent with at least a part of the garbage decaying benchmark information, wherein the garbage decaying benchmark information is used to determine whether the garbage in the garbage container has mold or odor.

The prompt information presenting module 53 may be configured to, when the first determining module 52 determines that the garbage has mold or odor, present prompt information that recommends removing contents from the garbage container.

The above embodiment of the device for presenting prompt information that recommends removing contents from a garbage container acquires garbage information and garbage decaying benchmark information in a current garbage bag by an acquiring module, determines whether garbage in the garbage container has mold or odor based on the garbage information and the garbage decaying benchmark information by a first determining module, and presents prompt information that recommends removing contents from a garbage container when it is determined that the garbage has mold or odor by a prompt information presenting module to enable the user to remove the garbage by, for example, change the garbage bag that holds the garbage in the garbage container. Because the embodiment prompts the user to remove the garbage in the garbage container when it is determined that garbage has mold or odor, the impact on human health and the pollution of surrounding environment by garbage container be reduced effectively and use experience of the user can be improved.

Figure 6A:
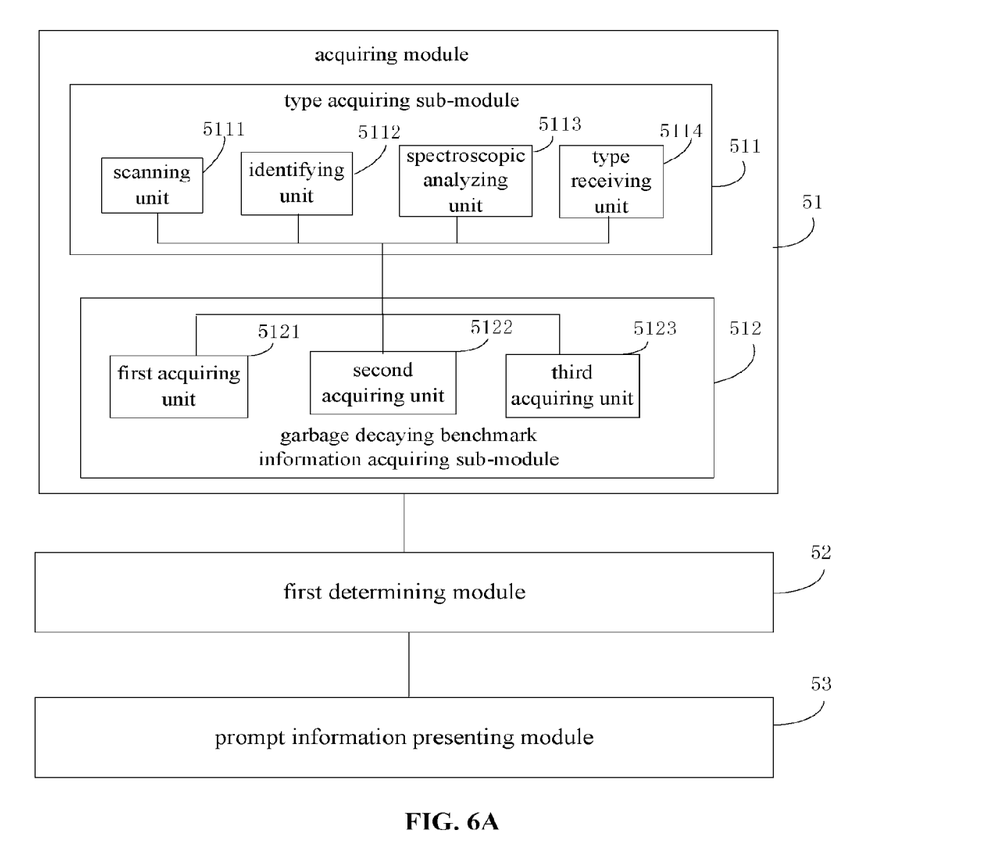
FIG. 6A is a block diagram showing another device for presenting prompt information that recommends removing contents from a garbage container according to an exemplary embodiment.

FIG. 6A is a block diagram showing another device for presenting prompt information that recommends removing contents from a garbage container according to an exemplary embodiment. As shown in FIG. 6A, based on the embodiment shown in FIG. 5, the acquiring module 51 may include: a type acquiring sub-module 511 and a garbage decaying benchmark information acquiring sub-module 512.

The type acquiring sub-module 511 may be configured to acquire a garbage type in the garbage container.

The garbage decaying benchmark information acquiring sub-module 512 may be configured to acquire garbage decaying benchmark information corresponding to the garbage type.

As shown in FIG. 6A, the type acquiring sub-module 511 may include one or more of the following: a scanning unit 5111, an identifying unit 5112, a spectroscopic analyzing unit 5113, or a type receiving unit 5114.

The scanning unit 5111 may be configured to acquire the garbage type by scanning a barcode on a packing box or on a packing bag of the garbage.

The identifying unit 5112 may be configured to acquire the garbage type by identifying the garbage via a camera.

The spectroscopic analyzing unit 5113 may be configured to acquire the garbage type by making a spectroscopic analysis on composition of the garbage.

The type receiving unit 5114 may be configured to receive the garbage type reported by the garbage container.

As shown in FIG. 6A, the garbage decaying benchmark information acquiring sub-module 512 may include one or more of the following: a first acquiring unit 5121, a second acquiring unit 5122, or a third acquiring unit 5123.

The first acquiring unit 5121 may be configured to query a database based on the garbage type to acquire garbage decaying benchmark information corresponding to the garbage type, the database storing decaying benchmark information of different garbage types.

The second acquiring unit 5122 may be configured to acquire garbage decaying benchmark information corresponding to the garbage type from stored history record information.

The third acquiring unit 5123 may be configured to acquire garbage decaying benchmark information corresponding to the garbage type based on user's review information.

The above embodiment of the device for presenting prompt information that recommends removing contents from a garbage container provides various ways to acquire a garbage type and provides various ways to acquire garbage decaying benchmark information based on the garbage type. As can be seen, the present embodiment may be implemented in various different ways with various modifications within the scope of the disclosure.

Figure 6B:
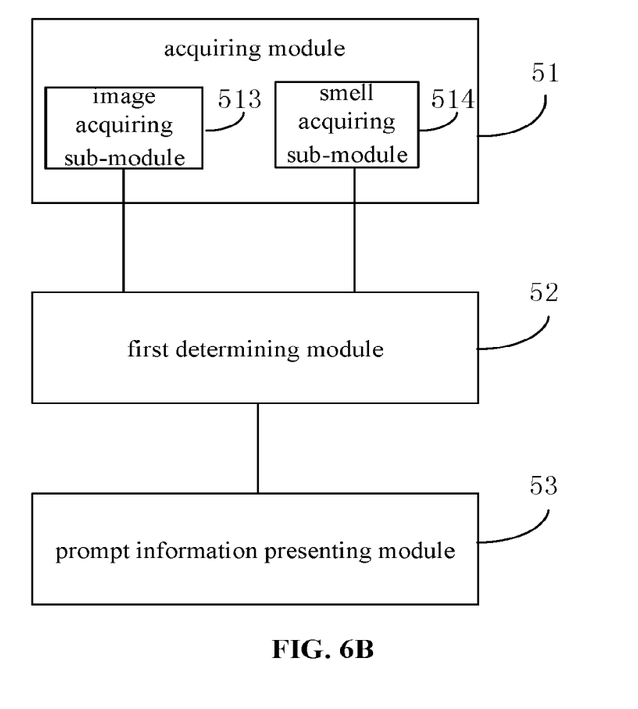
FIG. 6B is a block diagram showing another device for presenting prompt information that recommends removing contents from a garbage container according to an exemplary embodiment.

FIG. 6B is a block diagram showing another device for presenting prompt information that recommends removing contents from a garbage container according to an exemplary embodiment. As shown in FIG. 6B, based on the embodiment shown in FIG. 5, the acquiring module 51 may include at least one of an image acquiring sub-module 513 and a smell acquiring sub-module 514.

The image acquiring sub-module 513 may be configured to acquire garbage image information in the garbage container via a camera.

The smell acquiring sub-module 514 may be configured to acquire garbage smell information in the garbage container via a smell sensor.

The above embodiment of the device for presenting prompt information that recommends removing contents from a garbage container allows for subsequent operations by acquiring garbage information via a camera or a smell sensor.

Figure 7:
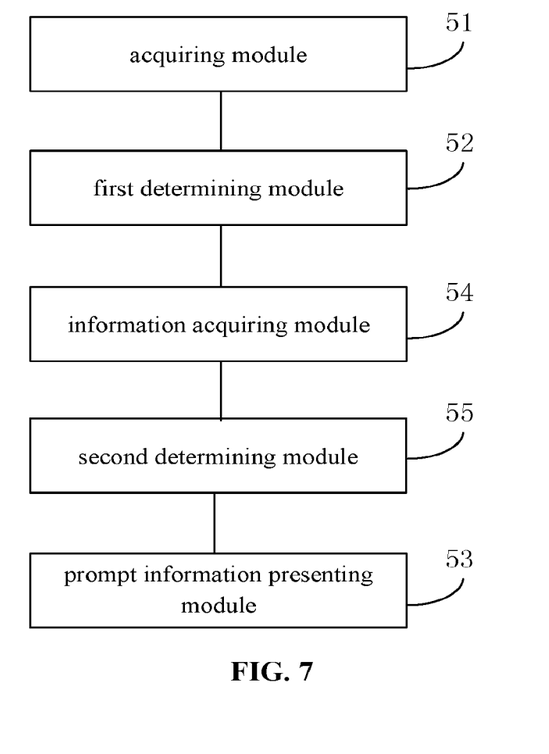
FIG. 7 is a block diagram showing another device for presenting prompt information that recommends removing contents from a garbage container according to an exemplary embodiment.

FIG. 7 is a block diagram showing another device for presenting prompt information that recommends removing contents from a garbage container according to an exemplary embodiment. As shown in FIG. 7, based on the embodiment shown in FIG. 5, the device may further include: an information acquiring module 54 and a second determining module 55.

The information acquiring module 54 may be configured to acquire behavior information of the user and a distance between the user and the garbage container, before the prompt information presenting module 53 presents the prompt information that recommends removing contents from a garbage container.

The second determining module 55 may be configured to determine whether the distance is smaller than a predetermined threshold and whether the behavior information is in a predetermined list, the predetermined list being used to store information of a behavior that can produce odor.

The above embodiment of the device for presenting prompt information that recommends removing contents from a garbage container can effectively reduce situations in which prompt information is presented to a user due to misjudgments, and thus effectively reduces interruption to users and improves the degree of use experience of the user.

Figure 8:
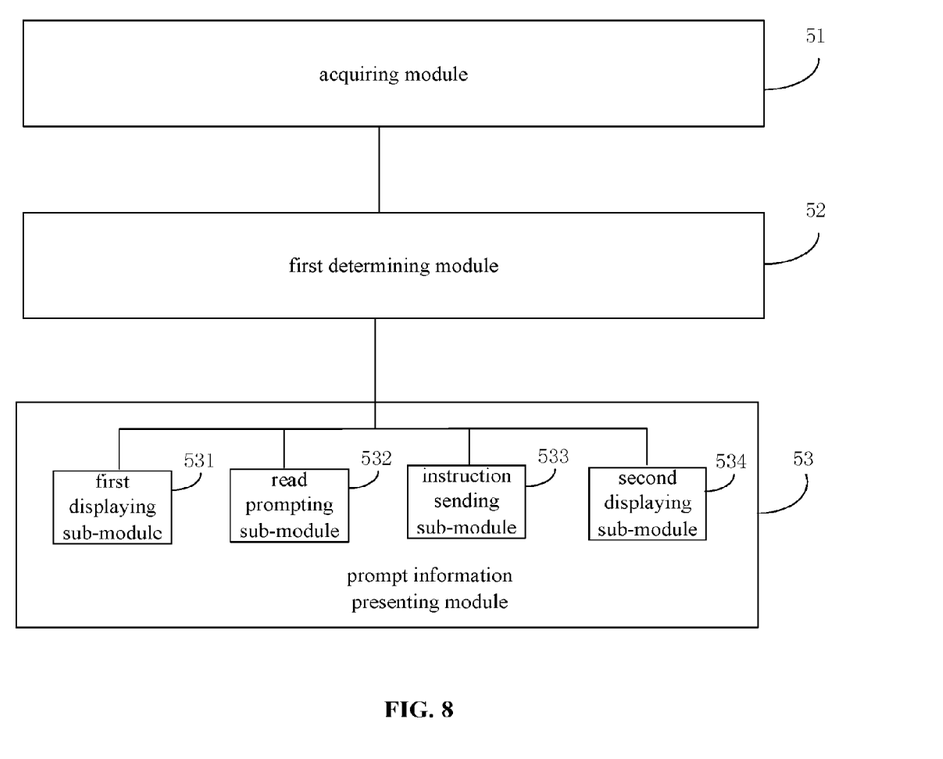
FIG. 8 is a block diagram showing another device for presenting prompt information that recommends removing contents from a garbage container according to an exemplary embodiment.

FIG. 8 is a block diagram showing another device for presenting prompt information that recommends removing contents from a garbage container according to an exemplary embodiment. As shown in FIG. 8, based on the embodiment shown in FIG. 5, the prompt information presenting module 53 may include one or more of the following sub-modules.

A first displaying sub-module 531 configured to display the prompt information that recommends removing contents from a garbage container via a mobile terminal.

A read prompting sub-module 532 configured to issue an alert via a wearable device indicating availability of the prompt information in order to prompt the user to read the prompt information.

An instruction sending sub-module 533 configured to, when it is detected that the mobile terminal is in the same local area network as the garbage container, send the garbage container a first instruction, which is used to control the garbage container to make a sound that recommends removing contents from a garbage container.

A second displaying sub-module 534 configured to, when it is detected that the mobile terminal is in the same local area network as the garbage container, display the prompt information that recommends removing contents from a garbage container via a terminal device, such as a TV, that is different form the mobile terminal.

The above embodiment of the device for presenting prompt information that recommends removing contents from a garbage container can present the prompt information in various ways, and can be implemented in flexible and diverse ways.

Figure 9:
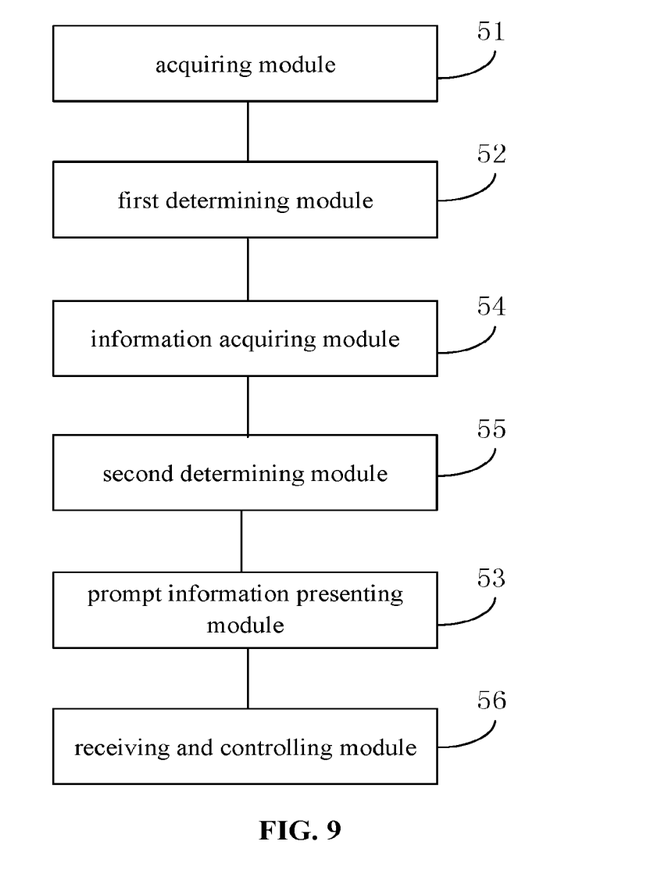
FIG. 9 is a block diagram showing another device for presenting prompt information that recommends removing contents from a garbage container according to an exemplary embodiment.

FIG. 9 is a block diagram showing another device for presenting prompt information that recommends removing contents from a garbage container according to an exemplary embodiment. As shown in FIG. 9, based on the embodiment shown in FIG. 5, the device may further include: a receiving and controlling module 56.

The receiving and controlling module 56 may be configured to, after the prompt information presenting module 53 presents the user the prompt information that recommends removing contents from a garbage container, receive a notification from the garbage container indicating that the contents corresponding to the prompt information have not been removed from the garbage container and send a smart device a second instruction used to control the smart device to handle the contents of the garbage container, such as to seal the garbage bag in the garbage container that holds the contents or to remove the garbage container.

By sending a second instruction to a smart device after receiving notification sent by the garbage container indicating that the contents have not been removed, the above embodiment of the device for presenting prompt information that recommends removing contents from a garbage container further enables the smart device to handle the contents of the garbage container, such as to seal the garbage bag or to remove the garbage bag, and thus effectively reduces the impact on human health and the pollution of surrounding environment by garbage.

With respect to the devices in above embodiments, specific manners in which respective modules and sub-modules perform operations have been described in detail in embodiments related to methods, which will not be elaborated herein.

It is noted that any one of the modules or sub-modules described in this disclosure can be implemented as hardware, software, or a combination of hardware and software. In an example, some or all of the modules or sub-modules in the FIGS. 5-9 are implemented as processing circuitry executing software instructions.

Figure 10:
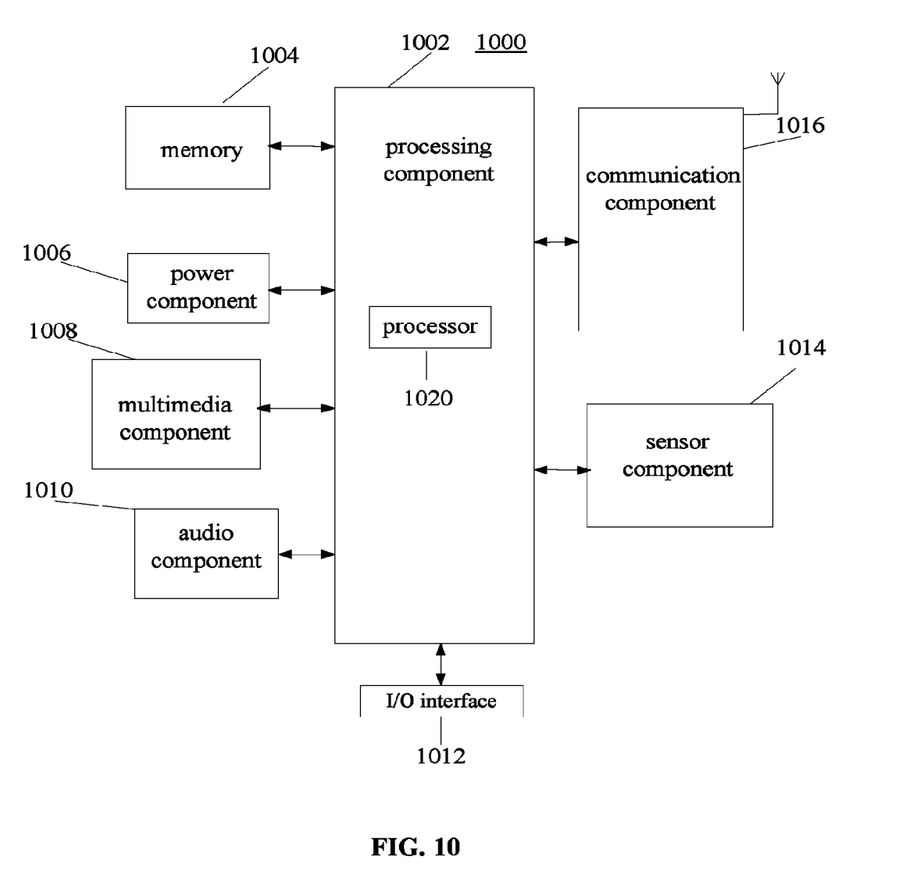
FIG. 10 is a block diagram applicable to a device for presenting prompt information that recommends removing contents from a garbage container according to an exemplary embodiment.

FIG. 10 is a block diagram applicable to a device for presenting prompt information that recommends removing contents from a garbage container according to an exemplary embodiment. For example, device 1000 may be a mobile phone, a computer, a digital broadcast terminal, a messaging device, a gaming console, a tablet, a medical device, exercise equipment, a personal digital assistant, an aircraft and the like.

Referring to FIG. 10, the device 1000 may include one or more of the following components: a processing component 1002, a memory 1004, a power component 1006, a multimedia component 1008, an audio component 1010, an input/output (I/O) interface 1012, a sensor component 1014, and a communication component 1016.

The processing component 1002 typically controls overall operations of the device 1000, such as the operations associated with display, telephone calls, data communications, camera operations, and recording operations. The processing component 1002 may include one or more processors 1020 to execute instructions to perform all or part of the steps in the above described methods. Moreover, the processing component 1002 may include one or more modules which facilitate the interaction between the processing component 1002 and other components. For instance, the processing component 1002 may include a multimedia module to facilitate the interaction between the multimedia component 1008 and the processing component 1002.

The memory 1004 is configured to store various types of data to support the operation of the device 1000. Examples of such data include instructions for any applications or methods operated on the device 1000, contact data, phonebook data, messages, pictures, video, etc. The memory 1004 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 1006 provides power to various components of the device 1000. The power component 1006 may include a power management system, one or more power sources, and any other components associated with the generation, management, and distribution of power in the device 1000.

The multimedia component 1008 includes a display providing an output interface between the device 1000 and the user. In some embodiments, the display may include a liquid crystal display (LCD) and a touch panel (TP). If the display includes the touch panel, the display may be implemented as a touch screen to receive input signals from the user. The touch panel includes one or more touch sensors to sense touches, swipes, and gestures on the touch panel. The touch sensors may not only sense a boundary of a touch or swipe action, but also sense a period of time and a pressure associated with the touch or swipe action. In some embodiments, the multimedia component 1008 includes a front camera and/or a rear camera. The front camera and the rear camera may receive an external multimedia datum while the device 1000 is in an operation mode, such as a photographing mode or a video mode. Each of the front camera and the rear camera may be a fixed optical lens system or have focus and optical zoom capability.

The audio component 1010 is configured to output and/or input audio signals. For example, the audio component 1010 includes a microphone ("MIC") configured to receive an external audio signal when the device 1000 is in an operation mode, such as a call mode, a recording mode, and a voice recognition mode. The received audio signal may be further stored in the memory 1004 or transmitted via the communication component 1016. In some embodiments, the audio component 1010 further includes a speaker to output audio signals.

The I/O interface 1012 provides an interface between the processing component 1002 and peripheral interface modules, such as a keyboard, a click wheel, buttons, and the like. The buttons may include, but are not limited to, a home button, a volume button, a starting button, and a locking button.

The sensor component 1014 includes one or more sensors to provide status assessments of various aspects of the device 1000. For instance, the sensor component 1014 may detect an open/closed status of the device 1000, relative positioning of components, e.g., the display and the keypad, of the device 1000, a change in position of the device 1000 or a component of the device 1000, a presence or absence of user contact with the device 1000, an orientation or an acceleration/deceleration of the device 1000, and a change in temperature of the device 1000. The sensor component 1014 may include a proximity sensor configured to detect the presence of nearby objects without any physical contact. The sensor component 1014 may also include a light sensor, such as a CMOS or CCD image sensor, for use in imaging applications. In some embodiments, the sensor component 1014 may also include an accelerometer sensor, a gyroscope sensor, a magnetic sensor, a pressure sensor, or a temperature sensor.

The communication component 1016 is configured to facilitate communication, wired or wirelessly, between the device 1000 and other devices. The device 1000 can access a wireless network based on a communication standard, such as WiFi, 2G, or 3G, or a combination thereof. In one exemplary embodiment, the communication component 1016 receives a broadcast signal or broadcast associated information from an external broadcast management system via a broadcast channel. In one exemplary embodiment, the communication component 1016 further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the device 1000 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above described methods.

In exemplary embodiments, there is also provided a non-transitory computer-readable storage medium including instructions, such as included in the memory 1004, executable by the processor 1020 in the device 1000, for performing the above-described methods. For example, the non-transitory computer-readable storage medium may be a ROM, a RAM, a CD-ROM, a magnetic tape, a floppy disc, an optical data storage device, and the like.

Other embodiments will be apparent to those skilled in the art from consideration of the specification and practice of the present disclosure. This application is intended to cover any variations, uses, or adaptations of the disclosed embodiments following the general principles thereof and including such departures from the present disclosure as come within known or customary practice in the art. The specification and embodiments are merely considered to be exemplary and the substantive scope and spirit of the disclosure is limited only by the appended claims.

It should be understood that the present disclosure is not limited to the exact structure as described above and shown in the figures, but can have various modification and alternations without departing from the scope of the disclosure. The scope of the disclosure is limited only by the appended claims.

What is claimed is:

1. A method for presenting prompt information that recommends removing contents from a garbage container, comprising:
    acquiring garbage information and garbage decaying benchmark information of the contents in the garbage container;
    determining whether the contents in the garbage container have mold or odor based on the garbage information and the garbage decaying benchmark information; and
    presenting the prompt information that recommends removing the contents from the garbage container when it is determined that the contents in the garbage container have mold or odor.

2. The method of claim 1, wherein acquiring garbage decaying benchmark information includes:
    acquiring a garbage type of the contents in the garbage container; and
    acquiring the garbage decaying benchmark information corresponding to the garbage type.

3. The method of claim 2, wherein acquiring the garbage type of the contents in the garbage container includes:
    acquiring the garbage type by scanning a barcode on a packing box or on a packing bag in the contents; or
    acquiring the garbage type by identifying the contents via a camera; or
    acquiring the garbage type by performing a spectroscopic analysis on composition of the contents; or
    receiving the garbage type reported by the garbage container.

4. The method of claim 2, wherein acquiring garbage decaying benchmark information corresponding to the garbage type includes:
    querying a database based on the garbage type to acquire garbage decaying benchmark information corresponding to the garbage type, the database storing decaying benchmark information of different garbage types; or
    acquiring garbage decaying benchmark information corresponding to the garbage type from stored history record information; or
    acquiring garbage decaying benchmark information corresponding to the garbage type based on user's review information.

5. The method of claim 1, wherein acquiring the garbage information of the contents in the garbage container includes:
    acquiring garbage image information of the contents in the garbage container via a camera; or
    acquiring garbage smell information of the contents in the garbage container via a smell sensor.

6. The method of claim 1, wherein determining whether the contents in the garbage container have mold or odor includes:
    determining whether the garbage information is consistent with at least a part of the garbage decaying benchmark information.

7. The method of claim 1, further comprising:
    acquiring behavior information of a user and a distance between the user and the garbage container,
    wherein presenting the prompt information is performed based on whether the distance is smaller than a predetermined threshold and whether the behavior information is in a predetermined list.

8. The method of claim 7, further comprising prohibiting presenting the prompt information when it is determined that the distance is smaller than the predetermined threshold and the behavior information is in the predetermined list.

9. The method of claim 1, wherein presenting the prompt information includes:
    displaying the prompt information via a mobile terminal; or
    issuing an alert via a wearable device, the alert indicating availability of the prompt information; or
    when it is detected that the mobile terminal is in the same local area network as the garbage container, sending the garbage container a first instruction, which instructs the garbage container to make a sound that recommends removing the contents from the garbage container; or
    when it is detected that the mobile terminal is in the same local area network as the garbage container, displaying the prompt information via a terminal device different from the mobile terminal.

10. The method of claim 1, wherein the method further includes:
    after presenting the prompt information that recommends removing the contents from the garbage container, receiving a notification from the garbage container indicating that the contents corresponding to the prompt information have not been removed from that garbage; and
    sending a smart device a second instruction that instructs the smart device to seal a garbage bag in the garbage container that holds the contents or to remove the garbage bag from the garbage container.

11. A device for presenting prompt information that recommends removing contents from a garbage container, comprising:
    a processor; and
    a memory storing instructions executable by the processor;
    wherein the processor is configured to
        acquire garbage information and garbage decaying benchmark information of the contents in the garbage container,
        determine whether the contents in the garbage container have mold or odor based on the garbage information and the garbage decaying benchmark information, and
        present the prompt information that recommends removing the contents from the garbage container when it is determined that the garbage have mold or odor.

12. The device of claim 11, wherein the processor is configured to
    acquire a garbage type of the contents in the garbage container, and acquire garbage decaying benchmark information corresponding to the garbage type.

13. The device of claim 12, wherein, when acquiring the garbage type of the contents in the garbage container, the processor is configured to
   acquire the garbage type by scanning a barcode on a packing box or on a packing bag in the contents, or
   acquire the garbage type by identifying the contents via a camera, or
   acquire the garbage type by performing a spectroscopic analysis on composition of the contents, or
   receive the garbage type reported by the garbage container.

14. The device of claim 12, wherein, when acquiring garbage decaying benchmark information corresponding to the garbage type, the processor is configured to:
   query a database based on the garbage type to acquire garbage decaying benchmark information corresponding to the garbage type, the database storing decaying benchmark information of different garbage types, or
   acquire garbage decaying benchmark information corresponding to the garbage type from stored history record information, or
   acquire garbage decaying benchmark information corresponding to the garbage type based on user's review information.

15. The device of claim 11, wherein, when acquiring the garbage information of the contents in the garbage container, the processor is configured to:
   acquire garbage image information of the contents in the garbage container via a camera; or
   acquire garbage smell information of the contents in the garbage container via a smell sensor.

16. The device of claim 11, wherein, when determining whether the contents in the garbage container have mold or odor, the processor is configured to:
   determine whether the garbage information is consistent with at least a part of the garbage decaying benchmark information.

17. The device of claim 11, wherein the processor is further configured to
   acquire behavior information of a user and a distance between the user and the garbage container,
   wherein presenting the prompt information is performed based on whether the distance is smaller than a predetermined threshold and whether the behavior information is in a predetermined list.

18. The device of claim 17, wherein the processor is configured to
   prohibit presenting the prompt information when it is determined that the distance is smaller than the predetermined threshold and the behavior information is in the predetermined list.

19. The device of claim 11, wherein, when presenting the prompt information, the processor is configured to
   display the prompt information via a mobile terminal, or
   issuing an alert via a wearable device, the alert indicating availability of the prompt information, or
   when it is detected that the mobile terminal is in the same local area network as the garbage container, send the garbage container a first instruction, which instructs the garbage container to make a sound that recommends removing the contents from the garbage container, or
   when it is detected that the mobile terminal is in the same local area network as the garbage container, display the prompt information via a terminal device different from the mobile terminal.

20. The device of claim 11, wherein the processor is further configured to
   after presenting the prompt information that recommends removing the contents from the garbage container, receive a notification from the garbage container, and
   send a smart device a second instruction that instructs the smart device to seal a garbage bag in the garbage container that holds the contents or to remove the garbage bag from the garbage container.

* * * * *